US005788653A

United States Patent [19]
Lorenzo

[11] Patent Number: 5,788,653
[45] Date of Patent: Aug. 4, 1998

[54] GUIDEWIRE EXTENSION WITH SLIDING RELEASE MECHANISM

[75] Inventor: Juan A. Lorenzo, Miami, Fla.

[73] Assignee: Cordis Corporation, Miami, Fla.

[21] Appl. No.: 627,308

[22] Filed: Apr. 3, 1996

[51] Int. Cl.$^6$ .................................................. A61B 5/00
[52] U.S. Cl. ........................... 600/585; 604/95; 604/96; 604/780
[58] Field of Search ........................... 128/772, 657, 128/658; 604/95, 96, 280, 281, 282, 283

[56] References Cited

U.S. PATENT DOCUMENTS

| | | |
|---|---|---|
| Re. 34,466 | 12/1993 | Taylor et al. . |
| 3,400,447 | 9/1968 | Woods, Jr. et al. . |
| 3,674,014 | 7/1972 | Tillander . |
| 4,003,369 | 1/1977 | Heilman et al. . |
| 4,045,859 | 9/1977 | Cooley et al. . |
| 4,068,660 | 1/1978 | Beck . |
| 4,538,622 | 9/1985 | Samson et al. . |
| 4,554,800 | 11/1985 | Moon . |
| 4,569,347 | 2/1986 | Frisbie . |
| 4,617,715 | 10/1986 | Koistinen et al. . |
| 4,771,500 | 9/1988 | Kovacs . |
| 4,827,941 | 5/1989 | Taylor et al. . |
| 4,846,193 | 7/1989 | Tremulis . |
| 4,875,489 | 10/1989 | Messner et al. . |
| 4,917,103 | 4/1990 | Gambale et al. . |
| 4,922,923 | 5/1990 | Gambale et al. . |
| 4,966,163 | 10/1990 | Kraus et al. . |
| 5,031,636 | 7/1991 | Gambale et al. . |
| 5,037,391 | 8/1991 | Hammerslag et al. . |
| 5,109,867 | 5/1992 | Twyford, Jr. . |
| 5,113,872 | 5/1992 | Jahrmarkt et al. . |
| 5,117,838 | 6/1992 | Palmer et al. . |
| 5,197,486 | 3/1993 | Frassica . |
| 5,247,942 | 9/1993 | Prather et al. . |
| 5,365,944 | 11/1994 | Gambale . |
| 5,421,348 | 6/1995 | Larnard . |

FOREIGN PATENT DOCUMENTS

| | | |
|---|---|---|
| 0347035 | 12/1989 | European Pat. Off. . |
| 2180454 | 4/1987 | United Kingdom . |

OTHER PUBLICATIONS

Constantin Cope, M.D., *Guide Wire Extension*, Sep. 24, 1985.

Primary Examiner—Max Hindenburg
Assistant Examiner—Pamela L. Wingood
Attorney, Agent, or Firm—Dean Garner

[57] ABSTRACT

In accordance with the present invention, there is provided a guidewire extension system which easily connects and disconnects the wires. The system includes a guidewire and an extension wire. Each wire has distal and proximal ends and a longitudinal axis therebetween. The distal end of the extension wire adapted to be releasably connected to the proximal end of said guidewire or vise-versa). The system further has a coiled spring mounted the distal end of the extension wire. The spring is adapted to receive the proximal end of the guidewire so that as the wires are puled apart, the spring constricts and grips the guidewire. Lastly, the system includes a tube disposed over the coiled spring. The tube is attached to the extension wire so that it slides along its longitudinal axis. The tube is adapted to engage and expand the spring as it is slid open, towards said proximal end of the extension wire, thereby releasing the guidewire wire.

8 Claims, 3 Drawing Sheets

5,788,653

GUIDEWIRE EXTENSION WITH SLIDING RELEASE MECHANISM

FIELD OF THE INVENTION

The present invention relates to a guidewire extension system. The invention has further relation to such a system which includes an extension wire having a connecting assembly at its distal end for releasably connecting a PTCA guidewire thereto, thereby enabling a balloon catheter to be removed and replaced with another balloon catheter.

BACKGROUND OF THE INVENTION

Guidewire extension systems for extending the length of steerable guidewires to effect a balloon catheter exchange are known in the art. Examples of such systems are disclosed in U.S. Pat. No. 5,113,872 issued to Jahrmarkt et al. on May 19, 1992, and U.S. Pat. No. 5,117,838 issued to Palmer et al. on Jun. 2, 1992, both of which are hereby incorporated herein by reference. Such devices use a coiled spring on the distal end of the extension wire which receives the proximal end of the guidewire. After the guidewire is inserted into the spring, the diameter of the spring will constrict and grip the guidewire as the two wires are pulled apart. The wires can thereafter be disconnected by rotating one or both of wires and pulling them apart.

Physicians often like to disconnect the extension wire from the guidewire after the catheter exchange is effected. It can often be cumbersome and awkward to manipulate the guidewire with the extension attached to it. However, it is also desirable to be able to reconnect the extension wire to the guidewire if another catheter exchange needs to be performed. Because of the small size of these wires, connection and disconnection of the wires can often be difficult. There is, therefore, a continuing desire to improve guidewire extension systems so that the wires can be even more easily connected and disconnected. The guidewire extension system of the present invention fulfills such a desire.

SUMMARY OF THE INVENTION

In accordance with the present invention, there is provided a guidewire extension system which easily connects and disconnects the wires. The system includes a guidewire and an extension wire. Each wire has distal and proximal ends and a longitudinal axis therebetween. The distal end of the extension wire is adapted to be releasably connected to the proximal end of the guidewire, or vise-versa. The system has a coiled spring mounted the distal end of the extension wire. The spring is adapted to receive the proximal end of the guidewire so that as the wires are pulled apart, the spring constricts and grips the guidewire. Lastly, the system includes a tube disposed over the coiled spring. The tube is attached to the extension wire so that it slides along its longitudinal axis. The tube is adapted to engage and expand the spring as it is slid open, towards the proximal end of the extension wire, thereby releasing the guidewire from the extension wire.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings wherein:

DETAILED DESCRIPTION OF THE INVENTION

Figure 1:
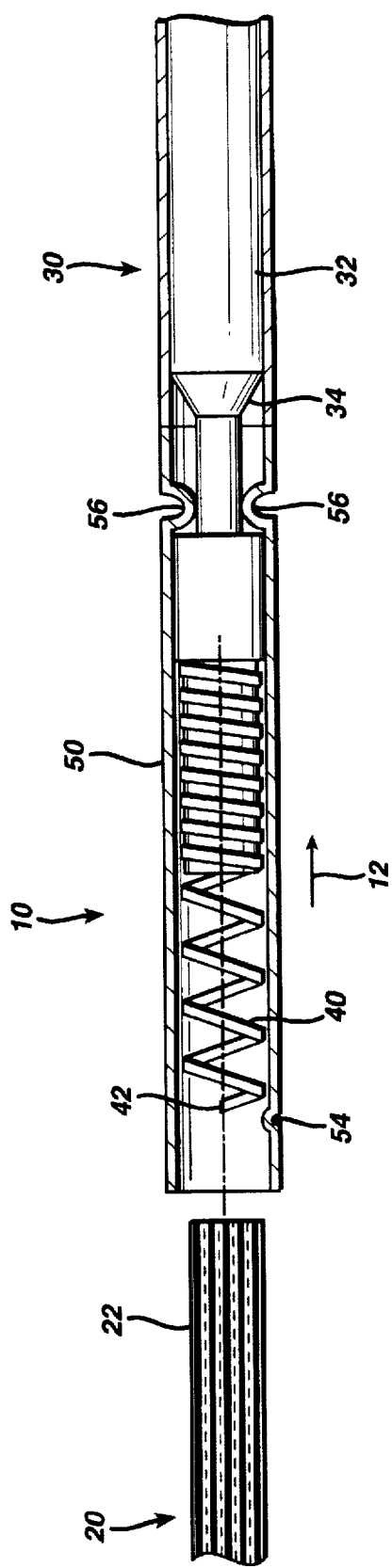
FIG. 1 is a simplified enlarged sectional view of the guidewire extension system of the present invention showing the proximal end of the guidewire and the distal end of the extension wire.

Referring now to the drawings in detail, wherein like numerals indicate the same element throughout the views, there is shown in FIG. 1 a guidewire extension system 10 in accordance with the present invention. System 10 includes a guidewire 20. Guidewire 20 is typically a steerable percutaneous transluminal coronary angioplasty (PTCA) guidewire such as that described in U.S. Pat. No. 5,267,574 issued to Viera et al. on Dec. 7, 1993 which is hereby incorporated herein by reference. Guidewire 20 has a distal end (not shown) which is inserted into the vascular system of a patient so as to guide a balloon catheter to a site of a stenosis or the like. Guidewire 20 also includes a proximal end 22 and a longitudinal axis running between the distal and proximal ends. System 10 further includes an extension wire 30. Extension wire 30 has a distal end 32, a proximal end (not shown), and a longitudinal axis running therebetween. As will be described herein, distal end 32 of extension wire 30 is adapted to be releasably connected to proximal end 22 of guidewire 20, or vise-versa.

System 10 has a coiled spring 40 mounted on distal end 32 of extension wire 30. The spring is typically about 1 inch in length and can be made from 304 V stainless steel or any other suitable material known to those skilled in the art. Spring 40 can be attached to the extension wire by resistance welding or any other suitable method known to those skilled in the art. As seen from FIG. 2, the spring is adapted to receive the proximal end of the guidewire. That is proximal end 22 of guidewire 20 is inserted within spring 40. Thereafter, as the wires are pulled apart, the spring constricts. That is the diameter of the coils decreases due the longitudinal expansion of the coil. This causes the spring to grip the guidewire, thereby connecting the guidewire to the extension wire. Preferably, coiled spring 40 comprises an open pitch flat wire coil having an internal diameter at its relaxed length which is slightly less than the outer diameter of proximal end 22 of guidewire 20. Therefore, when proximal end 22 of guidewire 20 is urged into coiled spring 40, spring 40 shrinks in its longitudinal length, causing the diameter of the coils to increase, i.e. the coil expands, to receive the guidewire. Typically coiled spring 40 has an internal diameter at its relaxed length of approximately 0.008 inch. Guidewire 20 typically has an outer diameter of approximately 0.013–0.014 inch. To keep the maximum diameter of system 10 between 0.013–0.014 inch, proximal end 22 of guidewire 20 is ground down to approximately 0.009 inch.

System 10 further includes a tube 50 disposed over the coiled spring. Tube 50 can be made from a hypotube, a metallic tube having a very thin wall which is typically used for hypodermic needles. Tube 50 can also be made from plastic, stainless steel or any suitable material known to those skilled in the art. The tube is attached to the extension wire so that it slides along the longitudinal axis of the extension wire. As seen from FIG. 3, the tube is adapted to engage and expand the spring as it is slid to its open position, which is towards the proximal end of the extension wire, in the direction of arrow 12. This action disconnects the guidewire from the extension wire. One way to effect this disengagement is to provide tube 50 with one or more detents or flanges 54 which engages spring 40 and both prevents the proximal end 42 of spring 40 from being moved out of tube 50 and engages the spring and allows it to expand when the tube is slid to its open position. Preferably, the tube 50 is gold plated, or is of a different color than that of the extension wire 30, to facilitate locating of tube 50 by a medical practitioner.

As seen from the figures, distal end 32 of extension wire 30 has a reduced diameter section 34 surrounded on either side by larger diameter sections. In addition, tube 50 has one or more flanges or notches 56 which are adjacent portion 34. These notches allow for the sliding movement of tube 50 to occur while preventing the tube from becoming loose from the extension wire.

Typically, when assembling system 10, spring 40 is placed over distal end 32 of extension wire 30 and resistance welded thereto. Tube 50 is then placed over spring 40 and distal end 32. Thereafter, tube 50 is deformed to create flanges 56.

Figure 2:
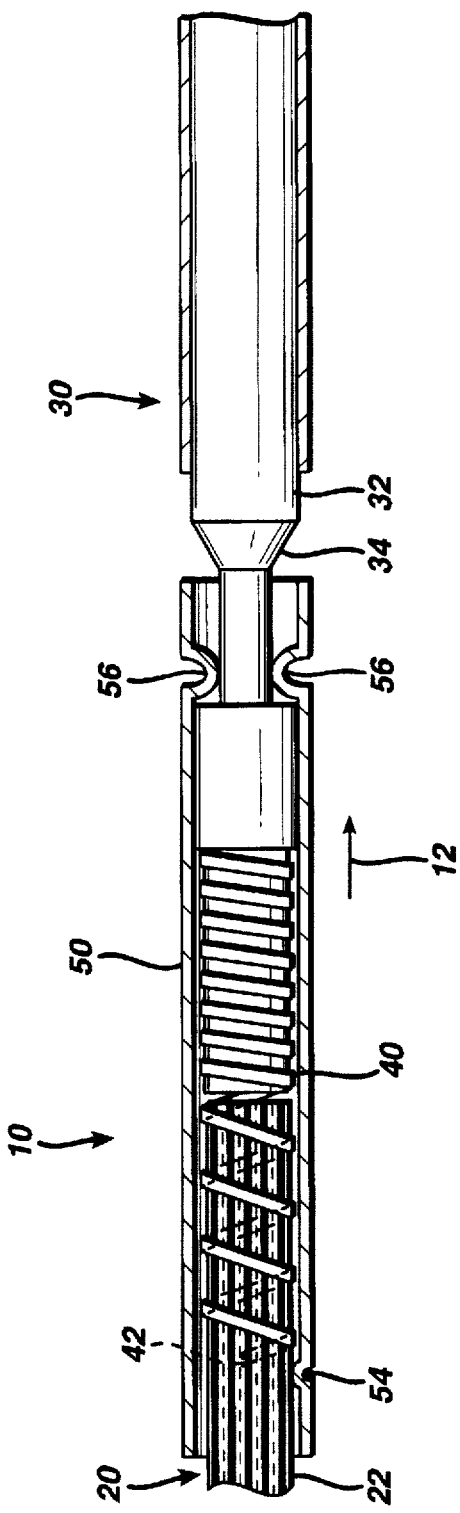
FIG. 2 is a view similar to that of FIG. 1, but showing the guidewire connected to the extension wire.
Figure 3:
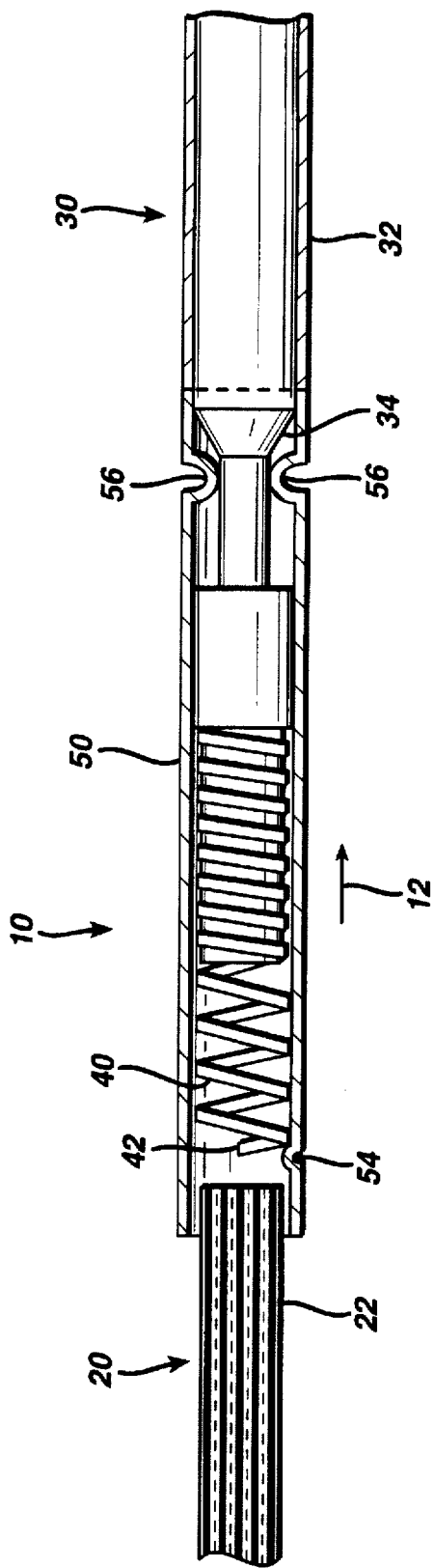
FIG. 3 is a view similar to that of FIG. 2, but showing the system after the guidewire has been released and with the tube in its open position.

In accordance with another aspect of the present invention, there is disclosed a method for connecting, and thereafter disconnecting, extension wire 30 to and from guidewire 20. As seen from FIG. 1, the method involves the steps of providing a length of extension wire 30 having a connecting assembly on its distal end comprising a small diameter tube 50 and a coiled spring 40 mounted in tube 50 and, thereafter, arranging the spring in the tube so that it can receive and grippingly engage proximal end 22 of guidewire 20. The method also involves providing a means for attaching the tube to the extension wire so that it slides along said longitudinal axis of said extension wire and providing tube 50 with a means for engaging and expanding the spring's inside diameter as it is slid open, towards the proximal end 32 of extension wire 30. Thereafter, as seen in FIG. 2, the method involves axially inserting proximal end 22 of guidewire 20 into coiled spring 40, thereby connecting distal end 32 of extension wire 30 to proximal end 22 of guidewire 20. Lastly, as seen in FIG. 3, the method involves sliding tube 50 along the longitudinal axis of extension wire 30 towards its proximal end, thereby expanding said coil and releasing said guidewire.

In accordance with yet another aspect of the present invention, there is provided a method of replacing a dilatation balloon catheter that was previously inserted on guidewire 30, through a guiding catheter and into a vascular system of a patient. Such method involves performing all of the method steps described in the preceding paragraphs and performing additional steps after the two wires are attached, but before they are disconnected. These additional steps include removing the initial dilatation balloon catheter over guidewire 20 and extension wire 30 and inserting a new dilatation balloon catheter over extension wire 30 and guidewire 20 and, thereafter, positioning the new balloon back into the vascular system of the patient.

Although particular embodiments of the present invention have been shown and described, modification may be made to the system without departing from the spirit and scope of the present invention. For example, it should be well understood by those skilled in the art that the position of the tube 50 and spring 40 can be reversed. That is, the tube and spring can be mounted on proximal end 22 of guidewire 20, and be adapted to receive the distal end 32 of extension wire 30. All of the terms used in describing the invention are used in their descriptive sense and not as terms of limitations.

What is claimed is:

1. A guidewire extension system comprising:

(a) a guidewire and an extension wire each having distal and proximal ends and a longitudinal axis extending therebetween;

(b) a coiled spring mounted on said distal end of said extension wire, said spring capable of receiving said proximal end of said guidewire and constricting and gripping said guidewire; and (c) a tube disposed over said coiled spring, said tube being slideably attached to said extension wire so that it slides relative to said extension wire and parallel to said longitudinal axis of said extension wire, said tube engaging said spring so that as said tube is slid open, towards said proximal end of said extension wire, said coil moves, expands and releases said guidewire.

2. The guidewire extension system of claim 1, wherein an interior of said tube includes a flange so that as said spring is slid open, said flange engages a distal end of said coiled spring thereby expanding said spring.

3. The guidewire extension system of claim 1 wherein said coiled spring comprises an open pitch flat wire coil having an internal diameter slightly less than the outer diameter of the proximal end of the guidewire so that, when the proximal end of said guidewire is urged into said coiled spring, said spring expands to receive said guidewire.

4. The guidewire extension system of claim 1 wherein said tube is of a different color than said extension wire.

5. A guidewire extension system comprising:

(a) a guidewire and an extension wire each having distal and proximal ends and a longitudinal axis extending therebetween;

(b) a coiled spring mounted on said proximal end of said guidewire, said spring capable of receiving said distal end of said extension wire and constricting and gripping said extension wire; and (c) a tube disposed over said coiled spring, said tube being slideably attached to said guidewire so that it slides relative to said guidewire and parallel to said longitudinal axis of said guidewire, said tube engaging said spring so that as said tube is slid open, towards said distal end of said guidewire, said coil moves, expands and releases said extension wire.

6. The guidewire extension system of claim 5, wherein an interior of said tube includes a flange so that as said spring is slid open, said flange engages a distal end of said coiled spring thereby expanding said spring.

7. The guidewire extension system of claim 5 wherein said coiled spring comprises an open pitch flat wire coil having an internal diameter slightly less than the outer diameter of the distal end of the extension wire so that, when the distal end of said extension wire is urged into said coiled spring, said spring expands to receive said extension wire.

8. The guidewire extension system of claim 5 wherein said tube is of a different color than said extension wire.

* * * * *